United States Patent [19]

Santangelo et al.

[11] Patent Number: 4,550,715
[45] Date of Patent: Nov. 5, 1985

[54] ENDOSCOPE INSERTION CANNULA ASSEMBLY

[75] Inventors: John A. Santangelo, East Freetown; Michael DiGiantommaso, Brockton, both of Mass.

[73] Assignee: Codman & Shurtleff, Inc., Randolph, Mass.

[21] Appl. No.: 544,680

[22] Filed: Oct. 24, 1983

[51] Int. Cl.$^4$ ................................................ A61B 1/06
[52] U.S. Cl. ........................................................ 128/4
[58] Field of Search ......................... 128/4, 5, 6, 7, 8, 9

[56] References Cited

U.S. PATENT DOCUMENTS

| | | | |
|---|---|---|---|
| 1,397,732 | 11/1921 | Goodloe | 128/7 |
| 1,880,551 | 10/1932 | Wappler | 128/7 |
| 2,584,619 | 2/1952 | Rubens et al. | 128/5 |
| 4,188,942 | 2/1980 | Fehlberg | 128/6 |
| 4,254,762 | 3/1981 | Yoon | 128/4 |

Primary Examiner—William H. Grieb
Attorney, Agent, or Firm—Donal B. Tobin

[57] ABSTRACT

A cannula including a guide and a cam housing rotatably supported about the guide into which a trocar obtuator and an endoscopy instrument may be inserted. A tapered proximal surface of the guide and a cooperating pin on the instrument rotate the instrument into proper rotational alignment. An axial slot extending from the distal end of the taper and a cooperating axial slot in the cam housing are aligned so that as the pin continues to slide axially into the cannula, the pin will interfere with a cam surface projecting from the side of the cam housing wall to rotate the cam housing out of the way as the pin proceeds further down the slot until the pin drops behind the cam surface into a pin retaining area. Thus, the instrument may be easily slid into the cannula, and through the action of the cam housing and guide, is held in proper axial, rotational and sealing alignment.

17 Claims, 10 Drawing Figures

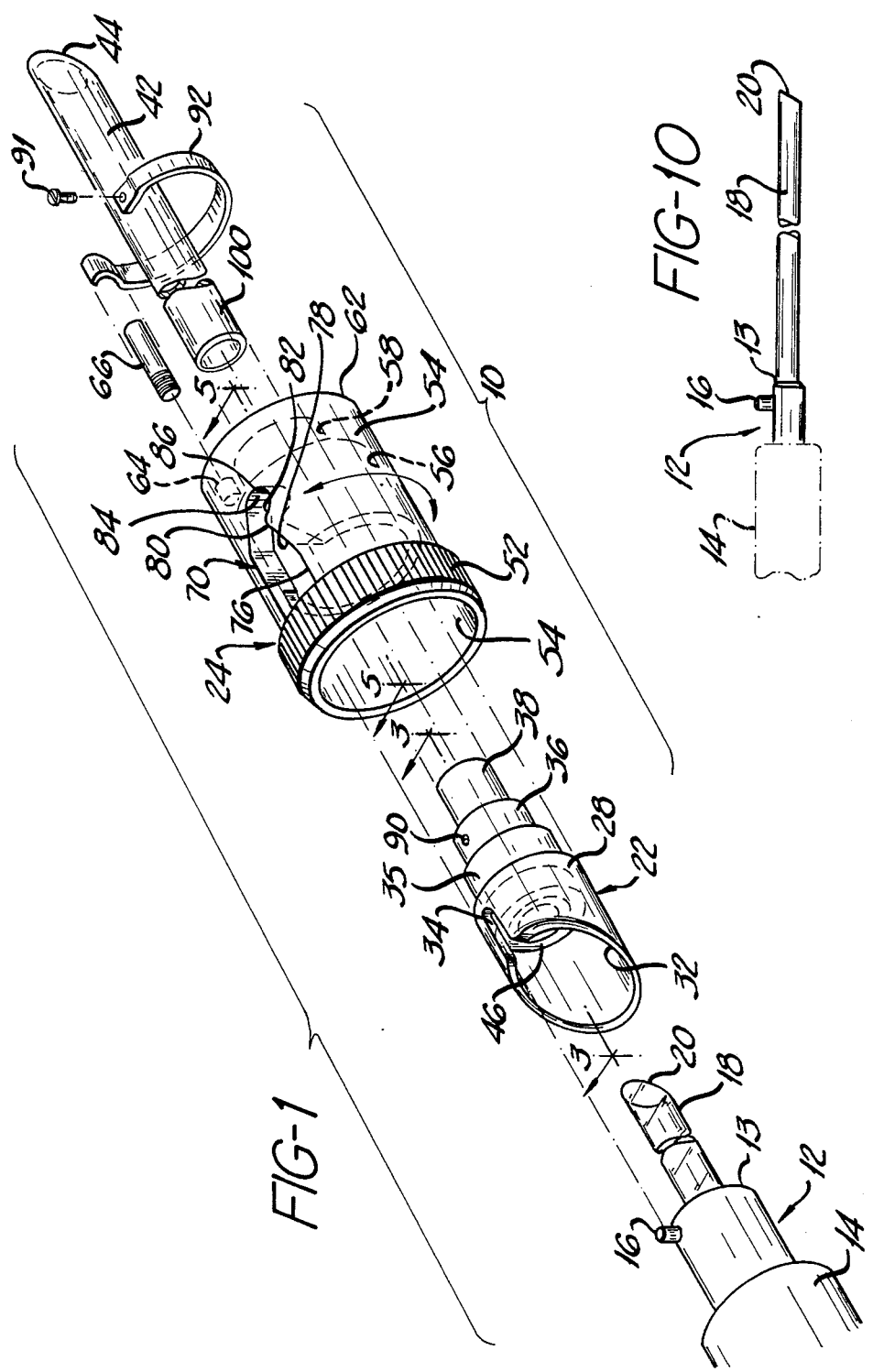

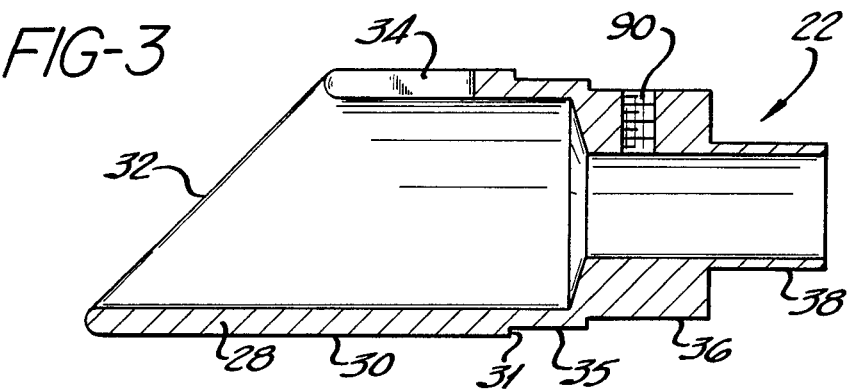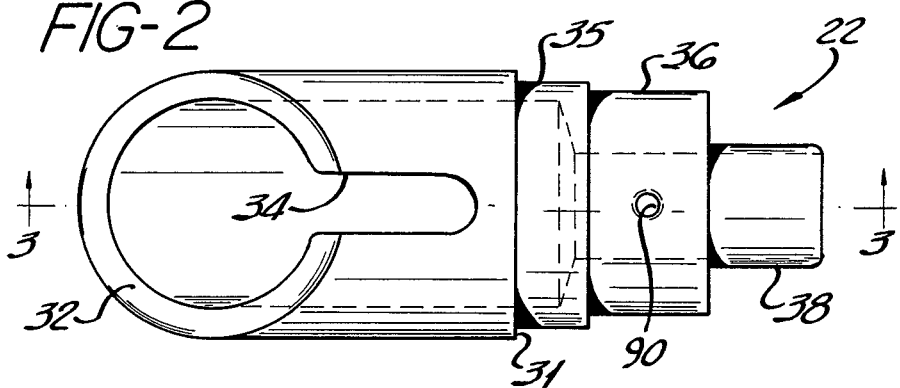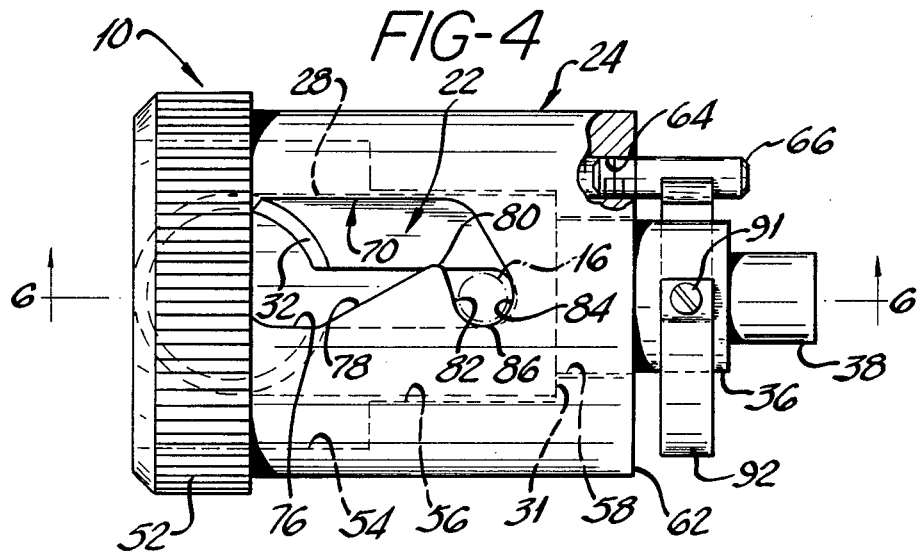

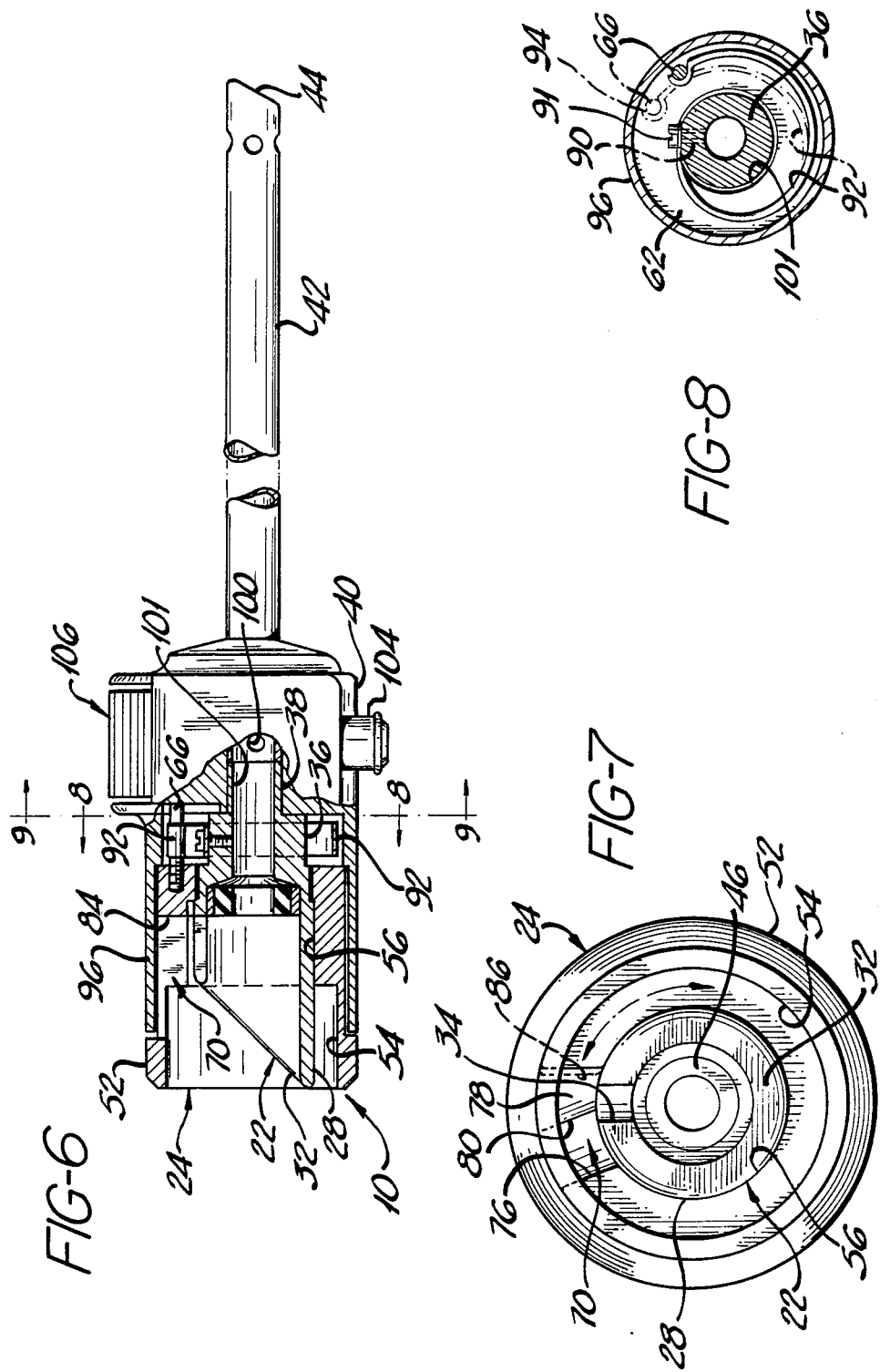

ENDOSCOPE INSERTION CANNULA ASSEMBLY

FIELD OF THE INVENTION

The present invention relates to a cannula assembly for inserting an endoscopy instrument into the body and more particularly to an insertion cannula with a locking mechanism for maintaining the endoscope in a desired rotational and axial position and a sealing mechanism for permitting irrigation or aspiration of the operative site.

BACKGROUND OF THE INVENTION

Endoscopy instruments may be inserted into the body by introducing them into a cannula which has previously been inserted through the skin using a conventional trocar. A cannula is a thin, hollow tube with an open tip on the distal end and a hub of expanded diameter on the proximal end. The hub acts as a guide for directing an instrument or a trocar into the lumen of the tube portion of the cannula. A trocar is an instrument whose sharpened tip projects a short distance beyond the distal end of a surrounding cannula tube. The cannula and the trocar form a small puncture wound in the body as they are inserted through the body tissue. The trocar is then removed leaving the cannula in position with its distal end located in a desired position in the body and with its proximal hub extending outside the body. Thus, the cannula provides an entry site for various endoscopy instruments into the body. A variety of surgical tools and appliances can be inserted through a cannula, for instance a surgical cutting instrument, an aspiration or irrigation tube, or various optical or fiber-optic viewing devices, for example, telescopes which permit the surgeon to inspect the interior of the body.

Particularly with viewing instruments, like telescopes, it is important that the orientation of the optical system inside the body be readily observable from outside the body. Very often the tip of the telescope is designed to look at an angle to its axis rather than straight ahead. The distal end of the telescope is placed at the distal end of the insertion cannula tube so that the telescope will be protected during use by the surrounding tip of the cannula tube, which is usually made of metal or a relatively hard plastic. The distal tip of the cannula tube is also cut at an angle corresponding to the angle of the telescope to permit side viewing. When this side viewing configuration is contemplated, it is important to have the telescope in proper rotational registration with the distal end of the cannula tube. Otherwise, the telescope will focus on the confronting surface of the protective cannula tube rather than at the body structures. It is, thus, important that the precise axial position of the end of the telescope and its rotational orientation be known and controllable.

It is also important to orient the telescope properly with respect to any light source that is inserted into the body so as to reduce glare and shadows.

It is also important in the operating room environment that the telescope or other endoscopy instrument can be easily inserted through the cannula and locked into position so that the surgeon will not have to spend valuable operating time adjusting and aligning the telescope or other instrument.

It is also desirable to have tight sealing engagement between the cannula assembly and the endoscopy instrument to permit irrigation or aspiration of fluid with respect to the operative site. It would be desirable to have an insertion cannula with a locking mechanism which would allow the surgeon to insert a endoscopic instrument, for example a telescope, quickly and easily and be assured that the telescope is in its proper rotational and axial position and that that position could be maintained without constant monitoring and adjusting.

SUMMARY OF THE INVENTION

The present invention provides an insertion cannula assembly with a locking mechanism for holding an endoscopy instrument in a desired orientation with respect to an insertion cannula tube. The locking mechanism orients the endoscopy instrument in a desired rotational orientation regardless of the rotational orientation of the endoscopy instrument before it is inserted into the cannula assembly and locks the instrument into its desired axial and rotational position to maintain that position during use. The locking mechanism also provides a tight fluid seal between the cannula assembly and the endoscope so that fluid may be aspirated from or irrigated into the operative site.

Endoscopy instruments are usually long, thin, axially-extending devices. For the present invention, it is necessary to place a position-controlling device on the endoscope, for example a pin projecting transverse to the axis of the endoscope and mounted in the vicinity of the proximal end of the endoscope and interacting with a slot on the cannula. Alternatively, the pin may be mounted on the cannula and the slot on the endoscope. In this patent application the word "proximal" will be used to indicate that portion of a device closest to the end which projects outside the body. The word "distal" will be used to describe that portion of the device closest to the end inside the body.

The cannula assembly of the present invention includes a locking mechanism, a hub or guide portion and a cannula tube extending distally from the guide portion into the operative site. The guide and cannula tube may be designed as a unitary piece or as two separate pieces mounted into supporting structures. As an endoscope is inserted in the axial direction in the guide and cannula tube, the guide operatively engages the endoscope pin. The guide will cause the pin and, therefore, the entire endoscope to rotate into a desired rotational orientation and then hold that desired rotational orientation as the instrument is inserted further into the guide to effect locking and sealing. Surrounding the guide is a spring biased locking mechanism for restraining the pin in its desired axial position. The locking device includes a cam housing with a cam surface biased in interfering relationship with the pin as it advances into the guide. The cam surface moves out of the way as the pin advances further into the guide and tends to return toward its original biased position as the pin reaches its desired maximum distal position.

The locking mechanism and the guide device are preferably hollow, generally cylindrical devices with a generally circular cross section. However, other cross sections such as ovals, rectangles or other multi-sided cross sections can be used.

The guide device can have a bias cut, proximal end and an axial slot extending from the distal portion of the bias cut so that the bias cut will guide the pin into the guide slot as the endoscopy instrument is inserted into the guide and cannula tube. The locking mechanism can include a cam housing placed coaxially about the exterior of the guide and rotatable about the guide. The cam housing includes an axial slot in its sidewall which includes a cam portion projecting into the slot and coacting with the pin to rotate the cam housing as the pin advances along the guide slot. The cam housing slot also has a restraining portion for holding the pin and, thus, the endoscopy instrument in its known axial orientation. A spring is provided to bias the cam housing with respect to the guide.

The guide and cannula tube may be mounted in a flow control housing through which irrigation or aspiration fluid may be circulated through the operative site. The guide also includes a fluid seal to prevent this fluid from leaking from the cannula assembly. These and other features and advantages of the present invention will become apparent from the following detailed description of the preferred embodiments taken in conjunction with the following drawings:

BRIEF DESCRIPTION OF THE DRAWINGS

FIG. 1 shows an exploded perspective of the cannula assembly of the present invention and an endoscopy instrument;

FIG. 2 shows a radial view of the guide of the present invention;

FIG. 3 shows a cross-sectional view of the guide in FIG. 2 taken along lines 3—3 in FIGS. 1 and 2;

FIG. 4 shows a radial view, partly in section, of the guide, locking mechanism and seal of the present invention;

FIG. 6 shows a cross-sectional view of the cannula assembly of the present invention taken along lines 6—6 in FIG. 4 and mounted to a flow control housing;

FIG. 7 shows a proximal end view of the assembly of FIG. 6;

FIG. 8 shows a cross-sectional view of the assembly of FIG. 6 taken along lines 8—8 in FIG. 6;

DETAILED DESCRIPTION OF THE PREFERRED EMBODIMENT

Figure 5:
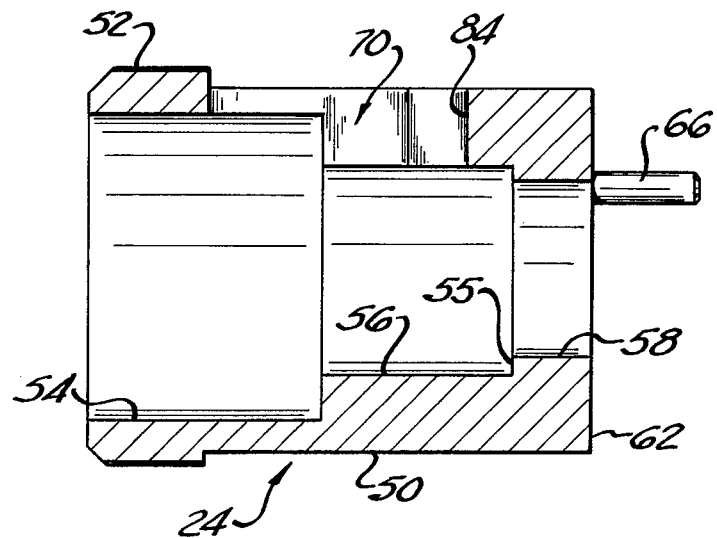
FIG. 5 shows a cross-sectional view of the cam housing of the present invention taken along lines 5—5 in FIG. 1.

Referring now to FIG. 1 there is shown an exploded perspective of the cannula assembly of the present invention, generally designated as 10, together with a endoscopy instrument 12. The endoscopy instrument 12, preferably a telescope, includes a proximal end fitting 14 to which is attached a pin 16 extending transversely to the longitudinal axis of the instrument 12. Pin 16 may be used as a stem to support a bearing to facilitate entrance into the locking mechanism of cannula assembly 10. Body 18 may be a flexible scope encased in a flexible sheath or a rigid scope encased in a rigid sheath. Instrument 12 is a viewing instrument, and the distal tip 20 of telescope body 18 is cut at a bias to facilitate side viewing. This bias tip may be cut at any convenient angle, but 30°, 45° or 60° is usually used.

Cannula assembly 10 of the preferred embodiment has four basic parts: a guide 22, a cannula tube 42, a cam housing 24, and a flow control housing 40 (shown in FIG. 6).

Guide 22 will now be described in detail in conjunction with FIGS. 1, 2, 3 and 5.

Guide 22 is a hollow, generally cylindrical piece with a surrounding sidewall 28, the outside surface of which is finished to provide a bearing surface 35. The proximal end surface 32 of guide 22 is bias cut at an angle to the axis of guide 22, for example 45°, and is preferably aligned along a plane which forms an angle of 45° with the axis of guide 22. Alternatively, end surface 32 need not be planar but could have a convex or concave curve. A slot 34 extends axially from the distal end of bias cut surface 32 a prescribed distance along surface 30. Surface 30 includes a step 31 which interacts with a corresponding step 55 on the interior surface of cam housing 24 to provide an axial stop for cam housing 24 with respect to guide 22.

Extending distally of the step 31 is a spring mounting portion 36 of guide 22, whose purpose will be described later in the application. Extending further distally from spring mounting portion 36 is a connection portion 38 for connecting guide 22 into a flow control housing 40, shown in FIGS. 6 and 9 whose purpose will be described later in the application.

Referring again to FIG. 1 a hollow cannula tube 42 extends from connection portion 38. Cannula tube 42 may be supported by suitable means, such as threading or press-fitting, into flow control housing 40 (shown in FIG. 6) to provide a path for inserting instrument 12 into the body. Flow control housing 40 will be described later in the application. The distal tip 44 of cannula tube 42 has a bias cut equivalent to the bias cut of tip 20 of telescope body 18. Instrument 12 is inserted through guide 22 until biased tip 20 extends just to the end of bias cannula tip 44 so that the bias portion of cannula tube 42 and telescope body 18 are aligned. This permits the surgeon to view the internal anatomy sideways through tip 20 of telescope body 18. It can be appreciated that it is important to have the tip 20 and tip 44 properly aligned, otherwise, the surgeon may be viewing the distally extending portion of tip 44 rather than the internal anatomy of the body.

An annular seat 46 (see FIG. 6) is placed within guide 22 to provide a tight fluid seal between guide 22 and surface 13 of instrument 12 so that, as will be explained later in greater detail, fluid introduced through flow control housing 40 will not leak past instrument 12 out of cannula assembly 10. Seal 46 may be a single rubber or plastic annulus or a steel annular bushing inside of which a rubber or plastic annulus is bonded. Other suitable sealing means may be used.

Careful axial alignment of the instrument 12 in cannula assembly 10 is important so that tip 20 is properly placed at the end of tip 44 and to effect a seal between sealing ring 46 and surface 13 of endoscope 12. Rotational alignment is important so that the biased tips 20 and 44 are properly aligned.

Referring now to FIGS. 1, 4 and 5, cam housing 24 will be described. Cam housing 24 is a hollow, generally cylindrical piece having sidewall 50. The proximal end of cam housing 24 has a radilly extending circumferential flange 52 to provide a means for manually rotating cam housing 24 about guide 22. Alternatively a separate annular ring may be formed as a separate part and joined cam housing 24.

The interior of cam housing 24 has three cylindrical surfaces 54, 56 and 58 of different diameters (see FIG. 5). Surface 54, placed at the proximal end of cam housing 24, has the largest interior diameter. Surface 58 has the smallest interior diameter and its interior surface is finished to provide a bearing surface cooperating with bearing surface 35 of guide 22 so that cam housing 24 may rotate about guide 22. Third surface 56 has a smaller internal diameter than surface 54 and its interior surface can be finished to provide a further bearing surface which cooperates with the confronting portion 30 of guide 22 and provides further bearing action for cam housing 24 to rotate about guide 22. Step 31 also provides an axial stop against step 55 for locating cam housing 24 in the correct axial position with respect to guide 22.

Radially extending distal end wall 62 of cam housing 24 has a bore 64 into which pin 66 may be press fit (see FIG. 4). Pin 66 acts as a retainer for a spring 92 (see FIGS. 6 and 8) to bias cam housing 24 with respect to guide 22 as will be explained subsequently in this application.

Referring again to FIG. 4, a cam slot 70 extends axially along sidewall 50 of cam housing 24 from the distal end of flange 52. Cam slot 70 can extend completely through sidewall 50 or can be recessed into the interior surface of sidewall 50. Cam slot 70 then extends axially a prescribed distance along sidewall 50 with the distal portion 84 of slot 70 positioned to act as a stop against which pin 16 will locate to control the distance which tip 20 of instrument 12 projects into cannula tube 42. Projecting from sidewall 76 of slot 70 is a cam surface 78 which forms a convenient angle, for example, 30° with the axis of cam housing 24. This angle can be any convenient angle and cam surface may be planar or may, in fact, have a concave or a convex curve to it. Cam surface 78 extends a predetermined axial distance along slot 70 to a peak 80 from which cam surface returns to side 76 of slot 70 along cam return surface 82. Cam return surface 82 is spaced apart from the distal end 84 of slot 70 a distance slightly greater than the diameter of pin 16 so as to form with the distal end 84 of slot 70 a pin retaining area. A portion of the distal end 84 of slot 70 is angled at a convenient angle to facilitate the movement of pin 16 into and out of slot retaining area 86.

Referring now to FIGS. 4, 6 and 7, guide 22 is shown inserted within cam housing 24. Bearing surfaces 35 of guide 22 fit in sliding bearing contact with surface 58 of cam housing 24 so as to provide a sliding bearing for the rotation of cam housing 24 about guide 22. It can be seen from FIGS. 4 and 6 that guide slot 34 aligns with sidewall 76 of cam slot 70 so that cam surface 78 projects across guide slot 34.

Referring now to FIG. 8, which is an end cross-sectional view of the assembly of FIG. 6, at section 8—8, the apparatus for biasing cam housing 24 with respect to guide 22 will now be described. Spring mounting portion 36 of guide 22 includes a tapped hole 90 in which one end of spring 92 may be mounted by means of a conventional fastener 91. Spring 92 is a generally circular piece of spring material which extends approximately 330° around a circle to its free end 94, which is formed as a clip to fit around pin 66. The spring action of spring 92 holds the free end 94 in proper position on pin 66. Spring 92 biases cam housing 24 rotationally with respect to guide 22 so that cam surface 78 is properly aligned with guide slot 34 of guide 22. It can be seen that as cam housing 24 is rotated counterclockwise in FIG. 8, spring 92 will coil so as to assume a smaller diameter. If cam housing 24 is released, spring 92 will return it to its original position.

Figure 9:
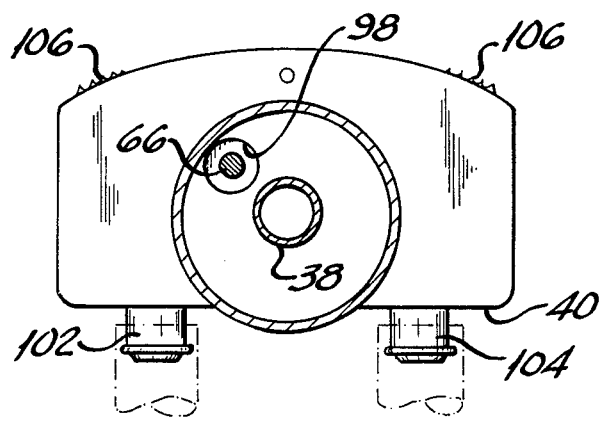
FIG. 9 shows an axial view of a flow control housing used with the cannula of the present invention; and, FIG. 10 shows a typical endoscopy instrument that can be used with the cannula assembly of the present invention.

Referring now to FIGS. 6 and 9 there is shown flow control housing 40 having a proximally extending flange 96 into which assembled cam housing 24 and guide 22 may be received and having a central opening 101 into which connection portion 38 of guide 22 may be press fit. Cannula tube 42 may also be press fit into housing 40 and abutted against the distal portion of connection portion 38. Flow control housing 40 has a recess 98 for receiving pin 66. Recess 98 has a diameter larger than pin 66 and acts as a stop to control the amount that spring pin 66 and, hence, cam housing 24 will rotate with respect to guide 22 under the influence of spring 92. Cannula tube 42 may have an opening 100 in its sidewall to permit the entry or exit of fluid into the interior lumen of cannula tube 42. Flow housing 40 includes fittings 102 and 104 for providing input and output of a fluid into the cavity of the body into which cannula assembly 10 has been inserted. The interior of flow control housing 40 is a hollow chamber for providing fluid communication between input 102 and output 104. A valve mechanism (not shown) may be controlled by switches 106 incorporated within flow control 40 for adjusting the flow or shutting it on and off.

The operation of cannula assembly 10 will now be described principally in connection with FIGS. 1 and 4. It can be seen that as endoscopy instrument 12 is inserted into guide 22, pin 16 will engage, biased, proximal end surface 32 of guide 22 and as instrument 12 is moved further axially, surface 32 and pin 16 will interact to rotate instrument 12 until pin 16 is aligned with guide slot 34. End surface 32 acts as an orienting mechanism for making sure that pin 16 and, hence, instrument 12 is aligned in its proper rotational orientation with guide slot 34 regardless of the orientation of instrument 12 when it is first inserted into guide 22. Referring now particularly to FIG. 4, one can see that just as pin 16 enters guide slot 34, it will begin to interfere with cam surface 78 of cam housing 24. Cam slot 70 and guide slot 34 are held in proper alignment by the action of spring pin 66 (which extends distally from cam housing 24) in recess 98 (in the confronting proximal surface of flow control housing 40). Pushing instrument 12 in the axial direction along guide slot 34 forces cam housing 24 to rotate downward in FIG. 4 until pin 16 has advanced axially along slot 34 to be aligned with peak 80 of cam surface 78. After pin 16 passes peak 80, it will engage cam return surface 82, and the action of spring 92 will return cam housing 24 to its original position and draw pin 16 into pin retaining area 86 of slot 70. Distal end surface 84 helps guide pin 16 into pin retaining area 86. Spring pin 66 will return to its correct rotational position because it is confined by recess 98. The geometry of the location of pin 16 with respect to tip 20 of instrument 12 and the location of pin retaining area 86 on cam housing 24 with respect to tip 44 of cannula tube 42 are properly chosen so that cannula tip 44 and instrument tip 20 are properly axially aligned. Thus, the cannula assembly 10 of the present invention provides proper rotational orientation and axial orientation of tip 20 with respect to tip 44. Return surface 82 also holds pin 16 so that surface 13 of endoscope 12 will tightly engage seal 46 to provide a fluid seal between endoscope 12 and guide 22.

It will be appreciated that instrument 12 can be quickly and easily inserted and locked into cannula assembly 10 using one hand motion and without having to pay any particular attention to the orientation of instrument 12 with respect to cannula assembly 10. Once instrument 12 is inserted into cannula assembly 10, it will be maintained in its proper axial and rotational orientations during use of endoscopy instrument 12.

In order to unlock and remove endoscopy instrument 12, the surgeon need only grasp flange 52 and rotate it and cam housing 24 downward in FIG. 4 and pull back on fitting 14 of instrument 12. The angled end surface 84 of slot 70 facilitates the removal of pin 16 from cannula assembly 10.

It will be noted that the diameters of pin 16, slot 34 and pin retaining area 86 are designed to fit closely together to provide a precise orientation for pin 16. For example, the diameter of pin 16 is 0.093 inches, the width of slot 34 is 0.098 inches and the width of pin retaining area 86 is 0.100 inches. It will also be appreciated that the end of slot 34 extends a short distance beyond the distal end 84 of slot 70 so that pin retaining area is defined by the confronting surfaces of the distal end 84 of slot 70, the side of slot 34 and the cam return surface 82.

It will be appreciated that the present invention provides a convenient and effective method of quickly introducing an endoscopy instrument into a cannula assembly and automatically providing correct and locked rotational and axial alignment for the instrument with respect to the tip of the cannula. The present invention has been described in conjunction with certain preferred embodiments. Those skilled in the art will appreciate that many modifications and changes may be made to the preferred embodiment without departing from the scope of the present invention. It is, therefore, not intended to limit the present invention except as set forth in the appended claims.

We claim:

1. A cannula assembly for inserting an endoscopy instrument through an opening into the body in a known orientation and for locking the instrument in that known orientation during use comprising:
   means affixed to an endoscopy instrument for controlling rotational orientation of said endoscopy instrument;
   guide means for receiving an endoscopy instrument and for operatively engaging said controlling means for placing said controlling means in a desired rotational orientation as said instrument is advanced into said guide means and for holding said desired orientation as said instrument advances further into said guide means regardless of the rotational orientation of said instrument when it is first inserted into said guide means;
   spring biased locking means for restraining said controlling means in a desired axial position including a cam surface biased in interfering relationship with said controlling means and adapted to move out of the way as said controlling means advances into said guide means and to return towards its original biased position as said controlling means reaches its desired axial position;
   to thereby position said instrument in its desired rotational orientation and to hold said instrument in its desired rotational and axial position during use.

2. The apparatus of claim 1 wherein said controlling means includes a pin extending transverse to the axis of said endoscopy instrument.

3. The apparatus of claim 1 wherein said guide means includes a hollow, generally cylindrical guide having a surrounding sidewall, a proximal end and a distal end, said guide adapted to axially receive said instrument, the proximal end of said guide being cut at a bias and having an axial slot extending from the distal portion of said bias cut end so that said bias cut, proximal end of said guide will guide said controlling means into said axial slot as said instrument is inserted into said guide so that the rotational orientation of said instrument is determined by the orientation of said axial slot regardless of the orientation of said controlling means when said instrument is first inserted into said guide.

4. The apparatus of claim 3 wherein said bias cut, proximal end of said guide includes a straight bias cut.

5. The apparatus of claim 1 wherein said locking means includes a hollow, generally cylindrical cam housing disposed coaxially about the exterior of said guide means and rotatable thereabout, said cam housing having a surrounding sidewall, a proximal end and a distal end;
   said sidewall of said cam housing having a generally axially extending cam slot therein, said cam slot including said cam surface and being adapted to cooperate with said controlling means to rotate said cam housing as said controlling means advances along said guide means and said cam slot having a controlling means restraining portion for holding said controlling means and thus said instrument in a known orientation;
   spring means for biasing said cam housing with respect to said guide means.

6. The apparatus of claim 5 wherein said cam surface includes a cam projection extending from one side of said cam slot into said cam slot, the interaction of said controlling means and said cam surface causing said cam housing to rotate with respect to said guide means as said controlling means advances into said guide means.

7. The apparatus of claim 5 wherein said cam housing slot extends completely through the sidewall of said cam housing.

8. The apparatus of claim 5 further including cooperating bearing surfaces disposed respectively on the interior of said cam housing and the confronting exterior surface of said guide means for providing a bearing surface along which said cam housing can rotate with respect to said guide means.

9. The apparatus of claim 5 further including stop means cooperatively engaging said controlling means for controlling the amount or rotation of said cam housing with respect to said guide means.

10. The apparatus of claim 5 wherein said cam slot has a distal end aligned at an angle to the axis of said cam housing and extending in the distal direction from said cam slot to said restraining portion to facilitate the removal of said controlling means from said restraining portion when said cam housing is rotated to unlock said locking mechanism.

11. The apparatus of claim 1 where said cam surface further includes a cam return surface adapted for interaction with said controlling means to urge said controlling means and, hence, said endoscopy instrument into its desired axial position in said cannula assembly.

12. A cannula assembly for inserting an endoscopy instrument through an opening into the body in known orientation and for locking the instrument in that known orientation during use comprising:
   a pin extending transverse to the axis of said instrument;
   a hollow, generally cylindrical guide having a surrounding sidewall, a proximal end and a distal end and said guide adapted to axially receive said instrument, the proximal end of said guide being cut at a bias and having an axial slot extending from the distal portion of said bias cut end so that said bias cut, proximal end of said guide will guide said pin into said guide slot as said instrument is inserted into said guide so that the rotational orientation of said instrument is determined by the orientation of said guide slot regardless of the orientation of said pin when it is first inserted into said guide;

a locking mechanism for said pin including a hollow, generally cylindrical cam housing disposed coaxially about the exterior of said guide and rotatable thereabout, said cam housing having a surrounding sidewall, a proximal end and a distal end;

said sidewall of said cam housing having a generally axially extending slot therein;

said cam housing slot including a cam surface adapted to cooperate with said pin to rotate said cam housing as said pin advances along said guide slot and having a pin restraining portion for holding said pin and thus said instrument in a known orientation;

spring means for biasing said cam housing with respect to said guide.

13. The cannula of claim 12 wherein said bias cut, proximal end of said guide includes a straight bias cut along a plane having a fixed angle with respect to the axis of said guide.

14. The cannula of claim 12 wherein said cam housing cam surface includes a cam projection extending from a sidewall of said cam housing slot into said cam housing slot, said cam projection adapted to interfere with said pin as said pin advances into said guide slot to rotate said cam housing with respect to said guide;

said cam projection extending along only a portion of said cam slot and said cam projection returning to the side of said cam slot from which it projects, said returning cam surface interacting with said pin to urge said pin and, thus, said instrument into its desired axial position in said cannula assembly; and, the confronting surfaces of said cam housing slot and said returning cam surface defining a pin retaining-portion of said cam slot for maintaining said pin in a desired axial position.

15. An assembly for permitting an endoscope instrument element to be inserted through a cannula element into the body in known orientation and for locking said cannula and said endoscope in that known orientation during use comprising:

means cooperatively disposed on said endoscopy instrument element and on said cannula element for controlling the rotational orientation and axial position of one element with respect to the other, said cooperative means including:

a protrusion on one of said cooperating elements;

a guide surface on said other element for operatively engaging said protrusion to control the axial position and rotational orientation of said protrusion;

spring biased locking means for restraining said protrusion in a desired axial position, said locking means including a cam surface biased in interfering relationship with said protrusion as said protrusion advances along said guide surface, said locking means adapted to move out of the way as said protrusion advances along said guide surface and to return towards its original position as said protrusion reaches its desired axial position;

to thereby position said instrument in its desired rotational orientation and to hold said instrument in its desired rotational and axial position during use.

16. The apparatus of claim 15, wherein said protrusion includes a pin mounted on one of said elements.

17. The apparatus of claim 15 wherein said guide surface includes a first portion extending at an angle the axis of said other element for rotating said protrusion to its desired rotational position as said endoscopy instrument element is advanced into said cannula element; and, a second portion forming a slot extending axially along said other element for defining said desired axial position of said protrusion with respect to said other element as said endoscopy instrument element is advanced into said cannula element.

* * * * *